United States Patent [19]

Nugent

[11] Patent Number: 5,000,804
[45] Date of Patent: Mar. 19, 1991

[54] PROCESS FOR MAKING BODY FLUID SAMPLE COLLECTION TUBE COMPOSITE

[76] Inventor: Edward L. Nugent, Ten Sheffield Rd., North Caldwell, N.J. 07006

[21] Appl. No.: 287,774

[22] Filed: Dec. 21, 1988

Related U.S. Application Data

[60] Division of Ser. No. 184,473, Apr. 21, 1988, abandoned, which is a continuation of Ser. No. 49,240, May 13, 1987, abandoned.

[51] Int. Cl.$^5$ ............................................. B32B 31/26
[52] U.S. Cl. .................................... 156/85; 156/86; 53/403; 53/405; 53/442; 128/760; 215/12.2
[58] Field of Search ............. 156/85, 86; 128/760, 128/764; 215/12.2; 53/403, 405, 442; 264/230, 342 R

[56] References Cited

U.S. PATENT DOCUMENTS

| | | | |
|---|---|---|---|
| 3,582,457 | 6/1971 | Barthell | 156/86 |
| 3,604,584 | 8/1971 | Shank | 156/86 |
| 3,698,586 | 10/1972 | Terner | 156/86 |
| 3,811,591 | 5/1974 | Novitch | 215/12.2 |
| 3,967,995 | 7/1976 | Fabianic | 156/86 |
| 4,016,704 | 4/1977 | Fujio | 156/86 |
| 4,016,706 | 4/1977 | Braker et al. | 156/86 |
| 4,225,049 | 9/1980 | Inoue | 215/12.2 |

*Primary Examiner*—Caleb Weston

[57] ABSTRACT

A composite body fluid sample container is provided which incorporates safety features for containing diseased samples of such fluids from touching and/or contaminating anyone handling the samples. The composite includes a glass sample container, either evacuated or not, depending upon use which has disposed thereon a "shrunk down" sleeve of a thermoplastic film. In the event that the glass is cracked or broken, the sleeve holds the sample from spilling or leaking onto the hands of a person handling the container, or otherwise spreading a diseased sample by spilling, leakage, or cutting by broken glass.

4 Claims, 1 Drawing Sheet

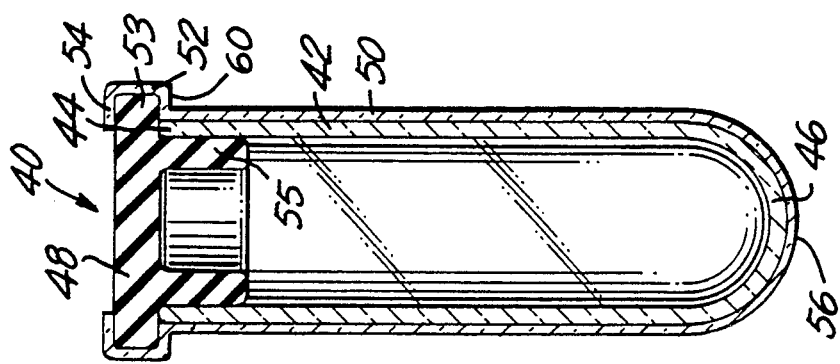
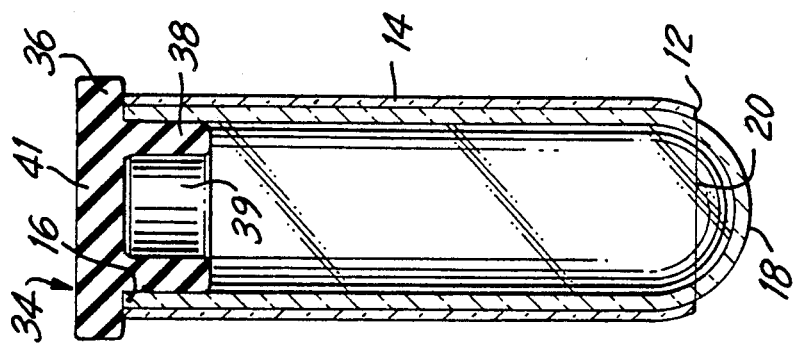
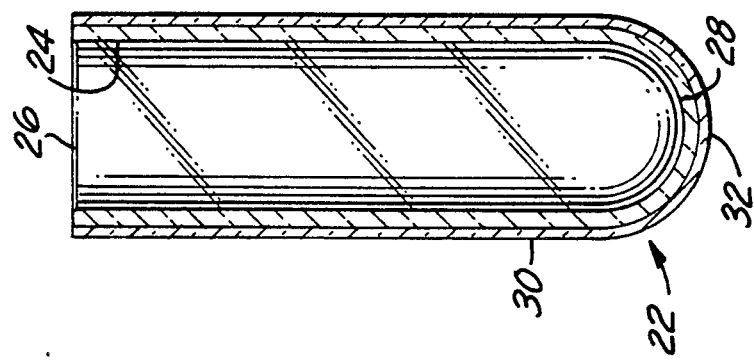
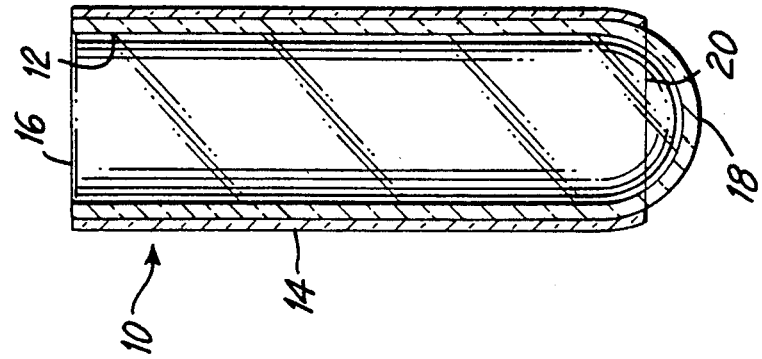

PROCESS FOR MAKING BODY FLUID SAMPLE COLLECTION TUBE COMPOSITE

This is a division of application Ser. No. 184,473, filed Apr. 21, 1988, abandoned, which is a continuation of application Ser. No. 049,240 filed May 13, 1987, now abandoned.

BACKGROUND AND STATEMENT OF THE INVENTION

This invention relates to containers for receiving body fluid samples, and for containing those samples for subsequent examination to determine the presence or absence of disease in the samples. Generally speaking, such containers will be in tube form and they may or may not be evacuated, depending upon the particular sample being taken. As will be understood by practitioners-inthe-art, evacuated tubes are used in great numbers for taking blood samples, with the tubes containing reagents for reacting with the blood samples for determining the presence or absence of disease. The tubes may also be non evacuated tubes for taking samples for one reason or another. Of course, urine samples may also be taken in both evacuated and non evacuated tubes. While non evacuated tubes are utilized in great numbers, it is preferred to use evacuated tubes for many specific applications for maintaining a seal of the tube prior to use and for facilitating the entry of the sample into the evacuated tube for subsequent testing of the sample.

For evacuated tubes, in particular, it is important to maintain the vacuum over a period of time in order to provide appropriate storage life for those tubes prior to their being used. That is, it is important for the vacuum level to be maintained for a period of time prior to the time when a technician or a nurse uses the tube for receiving a blood sample, for example. Many developments have been made in the past in order to provide plastic tubes for evacuated tube applications. However, plastic tubes have not been developed to the extent where they will maintain an appropriate vacuum for a period of time long enough to be satisfactory for a shelf-life which is appropriate under the circumstances in which such tubes are used. Therefore, it is appropriate and conventional for tubes to be comprised of glass for use as evacuated tubes because glass maintains the vacuum for a much longer or indefinite period of time.

The difficulty, on the other hand, with the use of glass tubes is breakage. With the advent of the highly contagious AIDS virus in many people, it has become extremely important to avoid contamination of technicians, nurses and doctors of blood samples obtained by them from diseased patients.

As will be understood, glass tubes break and/or they may be cracked by inadvertently being struck against some object during the course of the taking of a sample or the course of the sample being delivered from a patient to the laboratory for subsequent testing. It will be understood, further, that such breakage and/or cracking may result in leakage of a diseased blood sample, for example, over the hands of the technician or the person taking the sample or the laboratory technician who is in the course of examining the sample for the presence of disease. If that technician happens to have an open wound, the possibility of acquiring the AIDS virus, or some other disease such as hepatitis, is substantial. Also, broken glass may cut and contaminate, and the pieces must be handled in order to be disposed of. Accordingly, great pains are being taken in the development of any materials utilized for taking and handling samples which contain diseases of this kind and it is this situation to which this invention is particularly directed.

The invention herein utilizes a pre shrunk film disposed over the outer surface of a tube or other container for taking a body fluid sample. That is, a film is pre shrunk over the previously developed glass container. By having the entire outer surface, or a substantial portion thereof covered by a wrapped plastic film, if the tube is broken or cracked, in the kind of accident discussed above, the plastic wrap around the tube contains the sample therein. Thus, even though the sample may not be utilized for subsequent testing for the presence of disease because of the crack or break, at least the technician may contain the sample and dispose of it prior to any dripping or spilling and subsequent contamination. Also, the wrap will shield the user from sharp broken edges, and contains the shattered pieces of glass.

It will be understood, that it makes no difference whether the tube is evacuated or not evacuated in accordance with this invention. The presence of the film firmly adhering to the outer surface of the container holding the sample has the effect of maintaining the general integrity of the container holding a diseased sample so that it may be properly disposed of without any contamination to the user. In addition, the wrap makes the container stronger overall because of the cushioning characteristics of the wrap.

As purely illustrative of a plastic film material which may be used as a shrink wrap over a glass fluid specimen container, one may note that polyvinyl chloride, polyester copolymers or polystyrene films may be utilized for shrink wrapping such containers. One particularly appropriate material is polyvinyl chloride film such as "SkinTight" ®, a heat shrinkable polyvinyl chloride film supplied by Gilbreth International Corporation, Bensalem, Pa. 18020. Such polyvinyl chloride films obtain the desired shrinking property by first being extruded, and followed by then holding or restraining one dimension of the film while cooling the material, and not restraining the other dimension thereof. This has the effect of pre stressing the material in the direction in which it is held. Subsequently, with the application of heat, the material will then shrink about five to ten percent in the direction not held or restrained while shrinking about fifty five to seventy-five percent in the pre-stressed direction so that it "shrinks down" onto the vessel being covered.

It may be appropriate to apply a heat activated adhesive to the inner surface of the film which will adhere to the vessel being encompassed by the shrink-down film. The heat activated adhesive is printed or applied to the inner surface of the film and when the film is heated for shrinkdown onto the container, the adhesive becomes activated and helps adhere the film to the object being wrapped. Any conventional heat activated adhesive may be used for such application.

As a further feature of the invention, the shrunk down film may be applied to an evacuated container, for example, once the stopper therefor has been put into place and the vacuum applied, holding the stopper in a sealing position. Subsequent application of the plastic wrap which is to be shrunk down may be over both the container itself and it may extend up and over the stopper. By doing so, a further sealing of the stopper/tube interface takes place and a registered serration may be incorporated into the shrink film at the stopper/glass interface in order to develop a tamper proof closure. Such an arrangement may be appropriate, for example, in drug abuse testing, specimen identification and quality control.

Printing may be placed on either side of the shrinkable tube of film material which is to be shrunk down onto the container of interest. For example, a product identification, brand name, company logo may all be included on the inner or outer surface. Moreover, a matte finish or a corona discharged surface may be developed on the outer surface of the film to be shrunk onto the container so as to make the surface appropriate for writing identification information for a sample contained in the container. Furthermore, pressure sensitive adhesive labels may be placed on the outer surface of the shrunk down film so as to accommodate various hospital over labels, for example.

With the foregoing and additional objects in view, this invention will now be described in more detail, and other objects and advantages thereof will be apparent from the following description, the accompanying drawings, and the appended claims.

As purely illustrative of an arrangement of wrapped container which may be used for carrying out this invention, one may note the attached drawings in which several embodiments of such a container are shown utilizing the wrapped container feature of the invention.

IN THE DRAWINGS

FIG. 1 is a longitudinal sectional view of a tube-shaped body fluid sample container with the shrunk down wrap containing it, and illustrating one form of the invention;

FIG. 2 is a longitudinal sectional view of a tube shaped container with a pre shrunk film thereover illustrating an additional embodiment of the invention;

FIG. 3 is a longitudinal sectional view of the embodiment of FIG. 1 having a stopper placed in the open end thereof; and FIG. 4 is a longitudinal sectional view of a further embodiment of the invention illustrating a shrunk down evacuated tube structure with the stopper in place and with the film encompassing both the tube container and the stopper therefor.

DETAILED DESCRIPTION OF THE INVENTION

Referring to the drawings in which like reference characters refer to like parts throughout the several views thereof, FIG. 1 shows a tube 12, which may be plastic or glass, having an open end 16 and a closed end 18. This embodiment 10 shows a pre shrunk film 14 in the form of a tube extending over a substantial portion of the length of tube 12. As shown in FIG. 1, the tube shaped film 14 is shrunk into place and covers all of the tube 12 with the exception of the closed end 18 thereof. That is, the film 14 ends at the edge 20 thereof. Nevertheless, if the wall of tube 12 should be cracked or if the tube containing a sample should be dropped, the film will maintain the integrity of the tube for a period of time sufficient for allowing the user to dispose of the container with the contaminated sample.

Referring now to FIG. 2, a further embodiment 22 of the invention is shown having a glass tube 24 with an open end 26 and a closed end 28. Preshrunk over the entire glass tube 24 is a film 30 which, in this embodiment, is an enclosed tube shaped film which is shrunk down upon the entire outer surface of glass tube 24. This embodiment is more protective and sample containing in the event that tube 24 is broken in that the entire closed end 28 of tube 24 is covered as well as the side walls thereof. It will be understood by practitioners-in-the-art that the container integrity is substantially increased by this pre shrunk film so as to prevent spilling or leakage of a diseased sample contained in tube 24 from contaminating the user or a technician who may be handling the tube for examining the sample, for example.

FIG. 3 shows the embodiment of FIG. 1 with the stopper 34 therefor in place for closing the open end 16 of tube 12. As can be seen, stopper 34 includes an annular upper portion 36 which extends over the top edge of tube 12 as well as the top edge of the film 14. Stopper 34 includes a lower annular portion or skirt 38 which extends into and adheres to the inside walls of tube 12 for maintaining stopper 34 in place. Also, the annular lower skirt 38 of stopper 34 defines a well 38 which, in turn, defines a septum portion 41 of stopper 34 for receiving a needle therethrough. Thus, the user, once receiving a container such as that shown in FIG. 3 with a body fluid sample contained therein, may insert a needle through septum 41 for receiving part or all of the contents in container 12 to determine whether or not any disease is present in the sample.

In this connection, and as will be understood by practitioners-in-the-art, such tubes may contain reagents in the form of coatings on the inner surface of tube 12, for example or other forms of components for reacting with samples prior to their being tested to help determine the presence or absence of disease in that sample.

Referring now to FIG. 4, a further embodiment of contained body fluid sample container 40 is shown with a glass tube 42 having an open end 44 and a closed end 46. Disposed in tube 42 is stopper 48 having an annular upper flange 53 which extends over the top surface of the wall of tube 42 at the open end 44 thereof. Stopper 48 further includes a lower annular skirt 55 which adheres to the inner surface of the tube wall, as discussed above. This embodiment is different in that the tube is first evacuated with the simultaneous placement of stopper 48 therein followed by the application of a film sleeve 50 thereover. For this reason, the film sleeve 50 incorporates both the upper portion 53 of stopper 48, as well as the entire glass container tube 42. The shrunk fit film 50 includes serrations 60 at the tube 42, stopper 48 interface. The serrations are registered so that it can be determined if the sealed container has been tampered with. As discussed above, such an embodiment may be utilized, for example, for sealing the container with the stopper in place. Once a sample has been placed in the tube 42, the sample cannot be tampered with by removal of stopper 48 because the serrations 60 would determine that the sample had been tampered with. Such an arrangement may be utilized, for example, for drug abuse testing, specimen identification and quality control. It should be mentioned here that an embodiment such as that shown and described in FIG. 4, may be modified so that the film encompasses the stopper as shown in FIG. 4, and only a portion of the tube as shown in FIG. 1.

Thus, as will be apparent from the foregoing, there are provided in accordance with this invention safety containers for receiving and holding body fluid samples which may or may not contain disease. The arrangement herein of pre shrunk film covering the entire container is particularly appropriate for evacuated containers since glass tubes may then be used without the danger of cracking and/or breaking the container while it contains a disease containing body fluid sample. There is a substantial reduction in the possibility of contamination of the user under these circumstances. It will be understood, however, that the invention provides a very useful and inexpensive approach to containing samples in glass containers, whether or not the containers are evacuated.

Because of the tremendous concern in the spread of diseases such as hepatitis and AIDS, the arrangement herein is particularly useful for applications of the kind where the potential for spreading the disease is great, and particularly in obtaining blood samples in a series of evacuated tubes for subsequent transfer to a clinical lab for examination for the presence of such disease.

While the particular arrangements of body fluid samples disclosed herein form preferred embodiments of this invention, this invention is not limited to those particular embodiments and changes can be made therein without departing from the scope of the invention which is defined in the appended claims. For example, while the particular embodiments shown are all tube shaped, it will be understood that the shrinkable films of the invention herein may be arranged to conform to any configuration of container and the stopper or cap therefor. Thus, any form of container for holding fluids wherein glass is the preferred material may be used. Moreover, even though the film is particularly directed to increasing the integrity of a glass container it will be understood that the invention may be utilized for increasing the integrity of thin walled plastic containers as well.

What is claimed is:

1. A process for making a composite sample container assembly for receiving and containing disease bearing fluid samples without leakage, the steps which comprise
   (a) forming a glass container having an opening;
   (b) forming an elastomer stopper for said opening;
   (c) selecting a thermoplastic film;
   (d) applying, in a first applying step, a heat activated adhesive to the surface of said thermoplastic film which will face said glass container surface;
   (e) pre-stressing said thermoplastic film in one direction thereof in the presence of elevated temperatures;
   (f) evacuating said glass container for imparting a vacuum internally thereof while simultaneously seating said formed elastomer stopper in said opening of said glass container;
   (g) applying, in a second applying step, said pre-stressed film to at least the major portion of the outer surface of said glass container; and
   (h) shrinking down said film from step (g) into said glass container surface in the presence of elevated temperatures.

2. The process of claim 1, further characterized by
   (a) said glass container from step (a) is tube-shaped; and
   (b) said tube-shaped glass container having an open end and a closed end.

3. The process of claim 1, further characterized by
   (a) said film selected in step (c) is a member selected from the group consisting of polyvinyl chloride, polyester and polystyrene.

4. The process of claim 1, further characterized by
   (a) said applying step (e) includes applying said film over at least a portion of said elastomer stopper so that said film covers the glass container/stopper interface.

* * * * *